(12) United States Patent
Mathiaparanam

(10) Patent No.: US 6,429,341 B2
(45) Date of Patent: Aug. 6, 2002

(54) MODIFIER COMPOUNDS

(75) Inventor: Ponnampalam Mathiaparanam, Appleton, WI (US)

(73) Assignee: Appleton Papers Inc., Appleton, WI (US)

( * ) Notice: Subject to any disclaimer, the term of this patent is extended or adjusted under 35 U.S.C. 154(b) by 0 days.

(21) Appl. No.: 09/754,643

(22) Filed: Jan. 4, 2001

Related U.S. Application Data

(60) Provisional application No. 60/174,396, filed on Jan. 5, 2000.

(51) Int. Cl.⁷ .................... C07C 43/20; C07C 43/205; C07C 43/225
(52) U.S. Cl. ........................ 568/609; 568/610
(58) Field of Search .................. 568/609, 610

(56) References Cited

U.S. PATENT DOCUMENTS

| | | | |
|---|---|---|---|
| 4,531,140 A | 7/1985 | Suzuki et al. | 346/209 |
| 4,628,335 A | 12/1986 | Igarashi et al. | 346/208 |
| 4,649,160 A | 3/1987 | Machin | 514/652 |
| 4,659,643 A | 4/1987 | Ishida et al. | 430/157 |
| 4,855,278 A | 8/1989 | Igarashi et al. | 503/208 |
| 4,870,047 A | 9/1989 | Glanz et al. | 503/209 |
| 4,882,311 A | 11/1989 | Ikeda et al. | 503/208 |
| 4,888,321 A | 12/1989 | Kawakami et al. | 503/208 |
| 4,980,336 A | 12/1990 | Akutsu et al. | 503/209 |
| 4,981,835 A | 1/1991 | Iwakura et al. | 503/209 |
| 4,985,391 A | 1/1991 | Ikeda et al. | 503/208 |
| 5,041,604 A | 8/1991 | Saito et al. | 558/415 |
| 5,081,099 A | 1/1992 | Akutsu et al. | 503/209 |
| 5,091,359 A | 2/1992 | Ishida et al. | 503/209 |
| 5,143,890 A | 9/1992 | Tsuchida et al. | 503/201 |
| 5,164,357 A | 11/1992 | Bartman et al. | 503/209 |
| 5,179,068 A | 1/1993 | Goto | 503/209 |
| 5,242,884 A | 9/1993 | Mando et al. | 503/209 |
| 5,260,253 A | 11/1993 | Kawakami et al. | 503/216 |
| 5,312,950 A | 5/1994 | Boaz | 558/51 |
| 5,563,017 A | 10/1996 | Yabuki et al. | 430/138 |

FOREIGN PATENT DOCUMENTS

| | | | |
|---|---|---|---|
| DE | 3531125 C2 | | 3/1986 |
| EP | 0 873 880 A1 | * | 10/1998 |
| EP | 888906 A1 | | 1/1999 |
| EP | 0888906 A1 | | 1/1999 |
| GB | 2165953 A | | 4/1986 |
| JP | 403031233 A | * | 2/1991 |
| JP | 3169677 | | 7/1991 |
| JP | 03169677 A2 | | 7/1991 |
| JP | 4037583 | | 2/1992 |

OTHER PUBLICATIONS

American Chemical Society, CAS Registry No. 138569–83–2.
American Chemical Society, CAS Registry No. 143897–20–5.
American Chemical Society, CAS Registry No. 138569–83–2.
American Chemical Society, CAS Registry No. 138549–84–3.
American Chemical Society, CAS Registry No. 219511–45–2.
American Chemical Society, CAS Registry No. 138569–84–3.
American Chemical Society, CAS Registry No. 81549–83–9.
Tetrahedron Letters, vol. 30, No. 34 pp. 4509–4512, 1989 J. Ph. Soumillion, et al. No. 8796.850000.
American Chemical Society, CAS Registry No. 99700–23–9.
Mehrfach benzokondensierte Kronenether—Synthese, Ionenselektivitat in Membranelektroden und Wassereinschlub, E. Weber, Feb. 1985 No. 3160.000000.
American Chemical Society, CAS Registry No. 201041–89–6.

* cited by examiner

*Primary Examiner*—Rosalynd Keys
(74) *Attorney, Agent, or Firm*—Benjamin Mieliulis

(57) ABSTRACT

The present invention is a novel class of compounds useful in useful in thermally-responsive record material of the type comprising a substrate having provided thereon in substantially contiguous relationship an electron donating dye precursor, and an acidic developer material. The novel compound of the invention is a compound of the formula

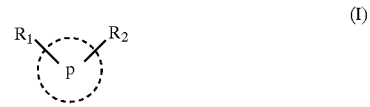

(I)

wherein P is selected from

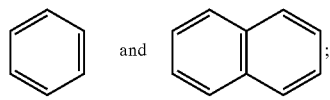

wherein $R_1$, is selected from hydrogen, alkoxy, and aralkoxy;

wherein $R_2$ is aralkoxyalkoxy when P is phenyl, and $R_2$ is selected from aralkoxyalkoxy or alkoxyalkoxy when P is naphthyl.

Said alkyl moieties are each independently from one to eight carbons, said aryl moieties each independently being unsubstituted or substituted by alkyl ($C_1$–$C_8$), alkoxy ($C_1$–$C_8$) or halogen.

The compounds of the invention enable manufacture of thermally responsive record material of the invention having the unexpected and remarkable properties of enhanced image intensity or density, and/or improved thermal response. The compounds of the invention also find use in diverse applications such as emolients and softening agents for creams, lots and cosmetics.

19 Claims, No Drawings

MODIFIER COMPOUNDS

This application under 35 USC § 111(a) claims benefit per 35 USC § 119(e) to application Ser. No. 60/174,396 filed Jan. 5, 2000 as a provisional application per 35 USC § 111(b)

BACKGROUND OF THE INVENTION

1. Field of the Invention

This invention relates to compounds useful in thermally-responsive record material. It more particularly relates to such record material in the form of sheets or rolls coated with color-forming material comprising chromogenic material (electron-donating dye precursor) and acidic color developer material. This invention particularly concerns compounds useful in making thermally-responsive record material (thermal record material) capable of forming a non-reversible image resistant to fade or erasure. The invention teaches new modifiers for record materials enabling manufacture of record materials having improved thermal response, image formation, image retention and/or image density.

2. Description of Related Art

Thermally-responsive record material systems are well known in the art and are described in many patents, for example U.S. Pat. Nos. 3,539,375; 3,674,535; 3,746,675; 4,151,748, 4,181,771; 4,246,318; and 4,470,057 which are hereby incorporated by reference. In these systems, basic chromogenic material and acidic color developer material are contained in a coating on a substrate which, when heated to a suitable temperature, melts or softens to permit the said materials to react, thereby producing a colored mark.

Thermally-responsive record materials have characteristic thermal responses, desirably producing a colored image upon selective thermal exposure.

In the field of thermally-responsive record material, thermal response is defined as the temperature at which a thermally-responsive material produces a colored image of sufficient intensity or density. The desired temperature of imaging varies with type of application of the thermally-responsive product and the equipment used in the imaging process. The ability to shift the temperature at which thermal image of sufficient intensity or density is produced for any given combination of chromogenic material and developer materials is a much sought after and very valuable feature. For example, recent advances in high speed text or image recording demand both high speed recording devices and corresponding thermally-responsive recording materials with sufficient thermal response that are capable of producing a high intensity or high density color image at low thermal energy.

Also, in the field of thermally-responsive record material, the ability to increase the efficiency of the thermal image formation process has decided advantages. First among these is the ability to obtain the same image intensity or density with lower amount of reactants or, alternatively, to obtain a more intense image with the same amount of reactants.

It is an object of this invention to provide a thermally-responsive material having enhanced image intensity or density and/or improved thermal response.

DETAILED DESCRIPTION

The present invention is a novel modifier compound for thermally-responsive record material. Such record material comprises a support having provided thereon in substantially contiguous relationship an electron donating dye precursor, an acidic developer material and a modifier compound.

The novel compound of the invention is a compound of the formula:

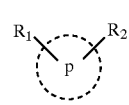
(I)

wherein P is selected from

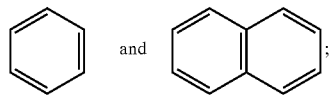

wherein $R_1$ is selected from hydrogen, aralkoxy and alkoxy;

wherein $R_2$ is aralkoxyalkoxy wherein P is phenyl, and $R_2$ is selected from aralkoxyalkoxy or alkylalkoxyalkoxy when P is naphthyl;

said alkyl moieties each independently being from one to eight carbons, said aryl moieties each independently being unsubstituted or substituted by alkyl ($C_1$–$C_8$), alkoxy ($C_1$–$C_8$) or halogen.

More particularly, when P is aryl, a novel class of modifiers is disclosed. In particular, the invention is an unsymmetrical phenyl compound of the formula:

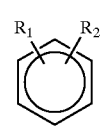
(II)

wherein $R_1$, is selected from hydrogen, alkoxy, and aralkoxy, wherein $R_2$ is aralkoxyalkoxy, said alkyl moieties each independently being from one to eight carbons, said aryl moieties each independently being unsubstituted or substituted by alkyl (($C_1$–$C_8$)), alkoxy ($C_1$–$C_8$) or halogen.

More particularly, when P is naphthalene, a novel class of modifiers is disclosed. In particular, the invention is an unsymmetrical naphthyl compound of the formula:

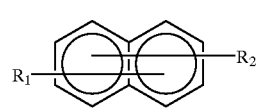
(III)

wherein $R_1$ is selected from hydrogen, alkoxy, aralkoxy;

wherein $R_2$ is aralkoxyalkoxy or alkylalkoxyalkoxy;

said alkyl moieties each independently being from one to eight carbons, said aryl moieties each independently being unsubstituted or substituted by alkyl ($C_1$–$C_8$), alkoxy ($C_{1-8}$) or halogen. For clarity, in structure III, $R_1$ and $R_2$ as shown should be understood as attached to either the same ring or the separate rings of the naphthyl structure.

Thermally responsive record material of the invention has the unexpected and remarkable properties of enhanced image intensity or density, and/or improved thermal response. The compounds disclosed herein as formula I, II or III desirably function as sensitizers or modifiers facilitating reaction between the mark forming components yielding a more intense image at lowered temperatures or faster imaging.

In the field of thermally-responsive record material, thermal sensitivity (response) is defined as the temperature at which a thermally-responsive material produces a colored image of satisfactory intensity (density). Background is defined as the amount of coloration of a thermally-responsive record material before imaging and/or in the unimaged areas of an imaged material. The ability to maintain the thermal sensitivity of a thermally responsive material while reducing the background coloration is a much sought after and very valuable feature.

These and other advantages are obtained from these compounds of the invention.

Increases in thermally-responsive material have been achieved through the incorporation of a sensitizing material in the color-forming composition along with the chromogenic material and acidic developer material. Examples of sensitizing materials are as follows: fatty acids such as stearic acid and behenic acid, amides of fatty acids such as stearamide, metallic salts of fatty acids such as zinc stearate, aluminum stearate, calcium stearate, zinc palmitate and zinc behenate, 4-benzylbiphenyl, triphenylmethane, benzyl 4-benzyloxybenzoate, 2-benzyloxynaphthalene, phenyl 2-naphthoate, 1,2-diphenoxyethane, 1,2-bis(3-methylphenoxy)ethane, 1,2-bis(4-methylphenoxy)ethane, 4-hydroxyoctadecanilide. The compounds of the invention are a new class of sensitizers or modifiers.

In addition to use in thermal record systems, the compounds of the invention also find use in such diverse applications as emollients and softening agents for creams, lotions and cosmetics.

Compounds illustrative of the invention according to formula I, II and III include without limitation:

A

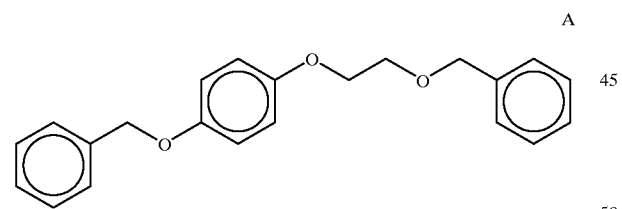

B

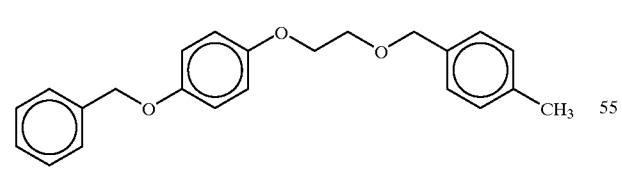

C

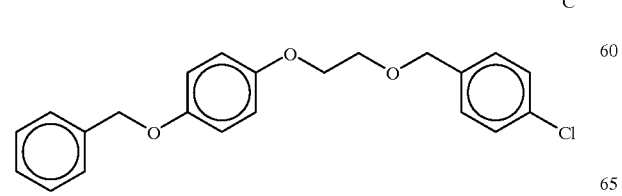

D

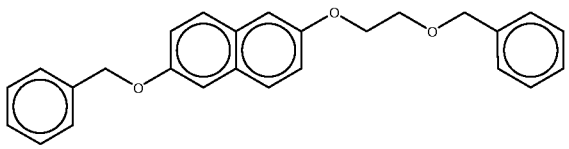

E

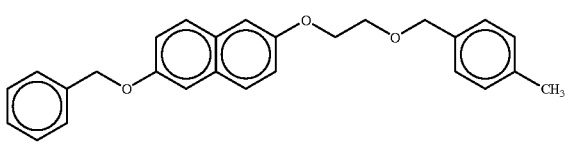

F

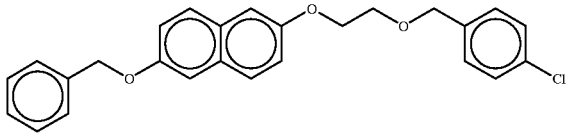

G

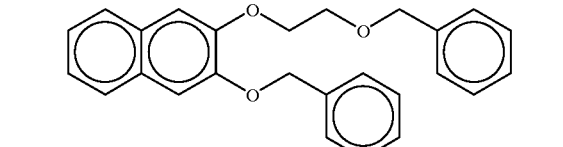

H

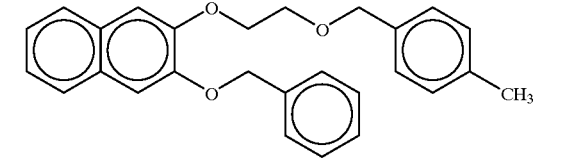

I

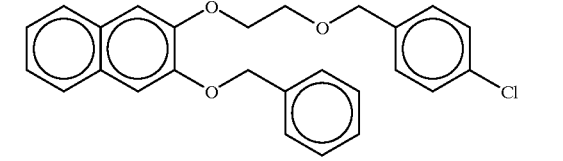

J

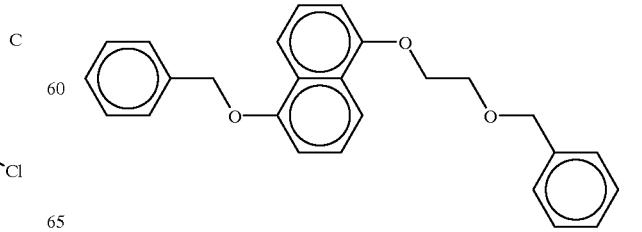

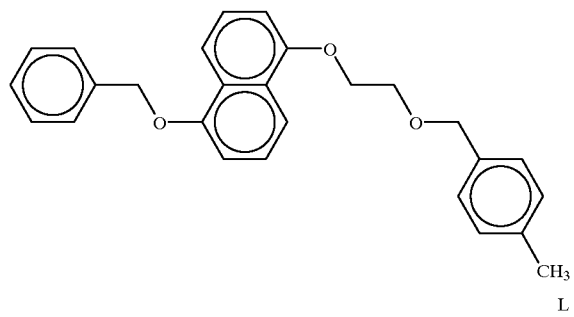

K

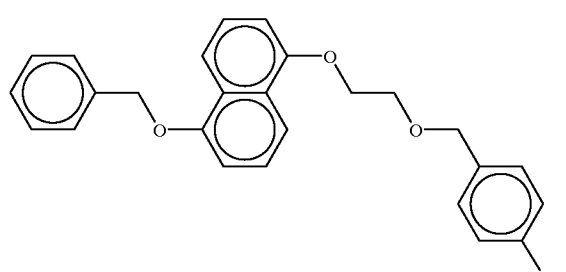

L

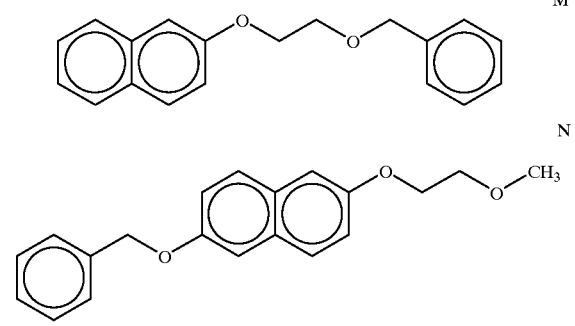

M

N

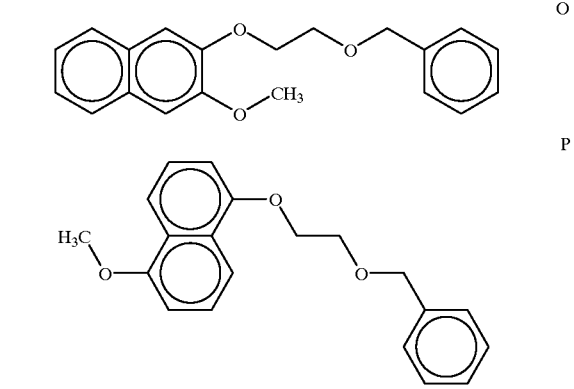

O

P

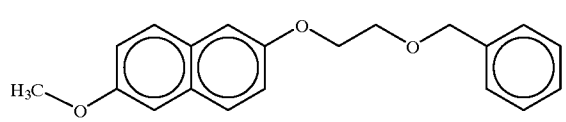

Q

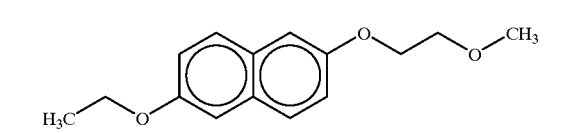

R

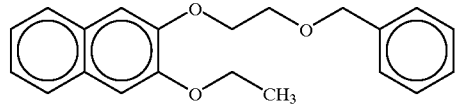

S

T

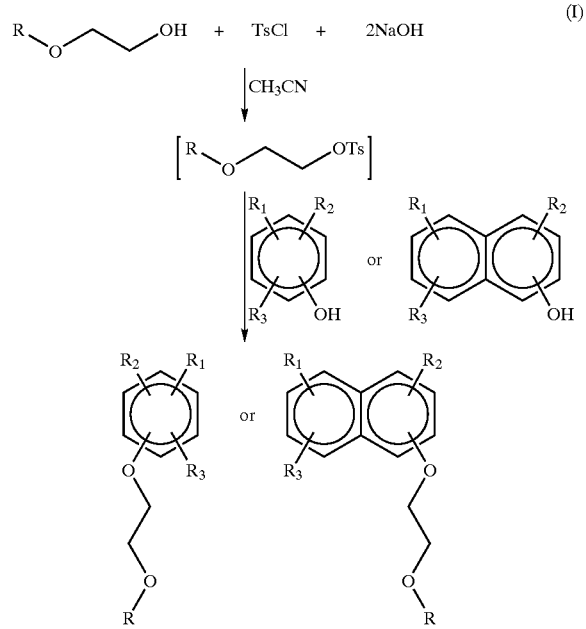

In general, the compounds according to formulas I, II or III can be synthesized from a corresponding substituted or unsubstituted benzyloxyalkanol or alkoxyalkanol.

The alcohol is first converted to tosylate using p-toluenesulfonyl chloride (TsCl) and aqueous sodium hydroxide in acetonitrile, keeping the temperature of the reaction mixture below about 55° C. by slow addition of the base. Then, the tosylate is reacted with the corresponding phenol at 80° C. for about five hours to give the final product.

The times and the temperatures in this general protocol are approximate, and the person skilled in the art can readily adjust the reaction conditions, depending on the moieties involved, to obtain the desired product.

More specific illustrative processes for synthesis of the specific compounds according to formulas I, II and III are set forth in more detail in synthesis example 1.

In the heat sensitive record material according to the invention, the compound according to formulas I, II or III is preferably used in an amount corresponding to 10 to 1000 parts by weight per 100 parts of the electron donating dye precursor though when blended with other sensitizers, the amount of the compound according to formulas I, II or III can optionally be used in reduced amounts.

The record material includes a substrate or support material which is generally in sheet form. For purposes of this invention, sheets can be referred to as support members and are understood to also mean webs, ribbons, tapes, belts, films, cards and the like. Sheets denote articles having two large surface dimensions and a comparatively small thickness dimension. The substrate or support material can be opaque, transparent or translucent and could, itself, be colored or not. The material can be fibrous including, for example, paper and filamentous synthetic materials. It can be a film including, for example, cellophane and synthetic polymeric sheets cast, extruded, or otherwise formed. The gist of this invention resides in the color-forming composition coated on the substrate. The kind or type of substrate material is not critical.

The components of the color-forming system are in substantially a contiguous relationship, substantially homogeneously distributed throughout the coated layer or layers of material deposited on the substrate.

The term substantially contiguous relationship is understood to mean that the color-forming components are positioned in sufficient proximity such that upon melting, softening or subliming one or more of the components, a reactive color forming contact between the components is achieved. As is readily apparent to the person of ordinary skill in this art, these reactive components accordingly can be in the same coated layer or layers, or isolated or positioned in separate layers. In other words, one component can be positioned in the first layer, and reactive or sensitizer components or the compound according to Formulas I, II or III, or an acidic developer or color former positioned in a subsequent layer or layers. The coating can optionally be applied to all of the substrate or spot printed on a certain portion. All such arrangements are understood herein as being "substantially contiguous."

Also, in the field of thermally-responsive record materials, there are well-known modifications in the coating structure. For example, a top-coating layer may be applied over a thermally-responsive layer as a protection for the latter, or a subcoating layer may be applied between the thermally-responsive layer and the support. Furthermore, some thermally-responsive record materials have both the topcoat and the subcoat in their design. The topcoat and subcoat may be either single-layered or multi-layered.

In manufacturing the record material, a coating composition is prepared which includes a fine dispersion of the components of the color-forming system, polymeric binder material, surface active agents and other additives in an aqueous coating medium. The composition can additionally contain inert pigments, such as clay, talc, aluminum hydroxide, calcined kaolin clay and calcium carbonate; synthetic pigments, such as urea-formaldehyde resin pigments; natural waxes such as Carnuba wax; synthetic waxes; lubricants such as zinc stearate; wetting agents; defoamers, and antioxidants. Other sensitizers can also be included. These sensitizers for example, can include acetoacetyl-o-toluidide, phenyl-1-hydroxy-2-naphthoate, 1,2-diphenoxyethane, and p-benzylbiphenyl or any of the sensitizing material listed earlier herein. Optionally, the record material can be topcoated or use subcoats such as insulating layers or hollow spheres. The color-forming system components are substantially insoluble in the dispersion vehicle (preferably water) and are ground to an individual average particle size of between about 1 micron to about 10 microns, preferably about 1–3 microns. The polymeric binder material is substantially vehicle soluble although latexes are also eligible in some instances. Preferred water soluble binders include polyvinyl alcohol, hydroxyethylcellulose, methylcellulose, methyl(hydroxypropyl) cellulose, starch, modified starches, gelatin and the like. Eligible latex materials include polyacrylates, styrene-butadiene-rubber latexes, polyvinylacetates, polystyrene, and the like. The polymeric binder is used to protect the coated materials from brushing and handling forces occasioned by storage and use of thermal sheets. Binder should be present in an amount to afford such protection in an amount less than will interfere with achieving reactive contact between color-forming reactive materials.

Coat weights can effectively be about 3 to about 9 grams per square meter (gsm) and preferably about 5 to about 6 gsm. The practical amount of color-forming materials is controlled by economic considerations, functional parameters and desired handling characteristics of the coated sheets.

Electron-donating dye precursors are also known as compounds. These electron donating dye cursors or chromogens include chromogenic compounds such as the phthalide, leucoauramine and fluoran compounds. These chromogenic materials or electron donating dye precursors are well known color-forming compounds for use in color-forming record systems. Examples of the compounds include Crystal Violet Lactone (3,3-bis(4-dimethylaminophenyl)-6-dimethylaminophthalide, (U.S. Pat. No. RE 23,024); phenyl-, indolyl-, pyrrolyl, and carbazolyl-substituted phthalides (for example, in U.S. Pat. Nos. 3,491,111; 3,491,112; 3,491,116; 3,509,174); nitro-, amino-, amido-, sulfonamido-, aminobenzylidene-, halo-, anilino-substituted fluorans (for example, the U.S. Pat. Nos. 3,624,107; 3,627,78; 3,641,011; 3,642,828; 3,681,390); spirodipyrans (U.S. Pat. No. 3,971,808); and pyridine and pyrazine compounds (for example, in U.S. Pat. Nos. 3,775,424 and 3,853,869). Other specifically eligible chromogenic compounds, not limiting the invention in any way, are: 3-diethylamino-6-methyl-7-anilino-flouran (U.S. Pat. No. 4,510,513); 3-dibutylamino-6-methyl-7-anilino-fluoran; 3-dibutylamino-7-(2-chloroanilino) fluoran; 3-(N-ethyl-N-tetrahydrofurfurylamino)-6-methyl-7-3,5'6-tris (dimethylamino)spiro[9H-fluorene-9,1'(3'H)-isobenzofuran]-3'-one; 7-(1-ethyl-2-methylindole-3-yl)-7-(4-diethylamino-2-ethoxyphenyl)-5,7-dihydrofuro[3,4-b] pyridin-5-one (U.S. Pat. No. 4,246,318); 3-diethylamino-7-(2-chloroanilino)fluoran (U.S. Pat. No. 3,920,510); 3-(N-methylcyclohexylamino)-6-methyl-7-anilinofluoran (U.S. Pat. No. 3,959,571); 7-(1-octyl-2-methylindole-3-yl)-7-(4-diethylamino-2-ethoxyphenyl)-5,7-dihydrofuro[3,4-b] pyridin-5-one; 3-diethylamino-7,8-benzofluoran; 3,3-bis(1-ethyl-2-methylindole-3-yl)phthalide; 3-diethylamino-7-anilinofluoran; 3-diethylamino-7-benzylaminofluoran; 3'-phenyl-7-dibenzylamino-2,2'-spirodi-[2H-1-benzopyran] and mixtures of any of the following.

Examples of eligible acidic developer material include the compounds listed in U.S. Pat. No. 3,539,375 as phenolic reactive material, particularly the monophenols and diphenols. Eligible acidic developer material also includes, without being considered as limiting, the following compounds which may be used individually or in mixtures: 4,4'-isopropylidinediphenol (Bisphenol A); p-hydroxybenzaldehyde; p-hydroxybenzophenone; p-hydroxypropiophenone; 2,4-dihydroxybenzophenone; 1,1-bis(4-hydroxyphenyl)cyclohexane; salicylanilide; 4-hydroxy-2-methylacetophenone; 2-acetylbenzoic acid;

m-hydroxyacetanilide; p-hydroxyacetanilide; 2,4-dihydroxyacetophenone; 4-hydroxy-4'-methylbenzophenone; 4,4'-dihydroxybenzophenone; 2,2-bis (4-hydroxyphenyl)-4-methylpentane; benzyl(4-hydroxyphenyl)ketone; 2,2-bis(4-hydroxyphenyl)-5-methylhexane; ethyl-4,4-bis(4-hydroxyphenyl) pentanoate; isopropyl4,4-bis (4-hydroxyphenyl) pentanoate; methyl-4,4-bis (4-hydroxyphenyl) pentanoate; alkyl-4,4-bis (4-hydroxyphenyl) pentanoate; 3,3-bis (4-hydroxyphenyl) pentane; 4,4-bis (4-hydroxyphenyl) heptane; 2,2-bis(4-hydroxyphenyl)-1-phenylpropane; 2,2-bis(4-hydroxyphenyl) butane; 2,2'-methylene-bis(4-ethyl-6-tertiarybutyl phenol); 4-hydroxycoumarin; 7-hydroxy-4-methylcoumarin; 2,2'-methylene-bis(4-octyl phenol); 4,4'-sulfonyldiphenol; 4,4'-thiobis(6-tertiarybutyl-m-cresol); methyl-p-hydroxybenzoate; n-propyl-p-hydroxybenzoate; benzyl-p-hydroxybenzoate. Preferred among these are the phenolic developer compounds. More preferred among the phenol compounds are 4,4'-isopropylindinediphenol, ethyl-4,4-bis(4-hydroxyphenyl)-pentanoate, n-propyl4,4-bis(4-hydroxyphenyl)pentanoate, isopropyl-4,4-bis (4-hydroxyphenyl) pentanoate, methyl 4,4-bis(4-hydroxyphenyl) pentanoate, 2,2-bis (4-hydroxyphenyl)-4-methylpentane, p-hydroxybenzophenone, 2,4-dihydroxybenzophenone, 1,1-bis(4-hydroxyphenyl) cyclohexane, and benzyl-p-hydroxybenzoate. Acid compounds of other kind and types are eligible.

Examples of such other compounds are zeolites, phenolic novolak resins which are the product of reaction between, for example, formaldehyde and a phenol such as an alkylphenol, e.g., p-octylphenol, or other phenols such as p-phenylphenol, and the like; and acid mineral materials including colloidal silica, kaolin, bentonite, attapulgite, hallosyte, and the like. Some of the polymers and minerals do not melt but undergo color reaction on fusion of the chromogen.

The following examples are given to illustrate some of the features of the present and should not be considered as limiting. In these examples all parts or proportions are by weight and all measurement are in the metric system, unless otherwise stated.

In all examples illustrated in the present invention, a dispersion of a particular system component was prepared by milling the component in an aqueous solution of the binder until a particle size of between about 1 micron and 10 microns was achieved. The milling was accomplished in an attritor or other suitable milling device. The desired average particle size was about 1–3 microns in each dispersion.

Although some of the examples illustrate the invention using 2,2-bis (4-hydroxyphenyl)4-methylpentane as the acidic developer material, the invention is readily practiced using any of the eligible acidic developer materials listed above.

The thermally-responsive sheets were made by making separate dispersions of chromogenic material, acidic material and the compound of formula I. The dispersions were mixed in the desired ratios and applied to a support with a wire wound rod and dried. Other materials such as fillers, antioxidants, lubricants and waxes can be added if desired. The sheets may be calendered to improve smoothness.

The thermal images are measured using a McBeth RD-922 densitometer. The densitometer is calibrated such that 0.08 indicates pure white and 1.79 a fully saturated black image.

Dispersions can be prepared in a quickie mill, attritor and small media mill. Optionally, but preferably dispersants can be added such as Nopco NDW at about 0.1 parts. This material is a sulfonated castor oil produced by Nopco Chemical Company. Surfynol 104 which is a di-tertiary acetylene glycol surface active agent produced by Air Products and Chemicals, Inc. could also be included, for example at about 0.4 parts. Additionally, water-soluble polymers other than polyvinyl alcohol (PVA) may be used to prepare the dispersions.

DESCRIPTION OF THE PREFERRED EMBODIMENTS

In the following example, a general procedure is described for preparing compounds according to the invention. The examples are not intended to be exhaustive and the moieties, as previously defined, are all eligible for use in any combination in preparing the compounds. Unless otherwise noted, all measurements, percentages and parts are by weight.

SYNTHESIS EXAMPLE 1

Preparation of 2-(Benzyloxy)ethyl-[4-(benzyloxy) phenyl]ether (Compound A)

2-(Benzyloxy)ethanol (61.0 g, 0.4 mole, and p-toluenesulfonyl chloride (80.0 g, 0.4 mole) were added with stirring to acetonitrile (20 ml) in a litre, four-necked, round-bottom flask, equipped with a mechanical stirrer, reflux condenser, thermometer and a dropping funnel. Aqueous sodium hydroxide (40.0 g, 1.0 mole/80 ml of water) was added slowly from the dropping funnel while the temperature of the reaction mixture was kept below 55° C. After the addition was complete, the reaction mixture was stirred for one hour as it cooled to room temperature. Then, 4-(benzyloxy)phenol (80.0 g, 0.4 mole) was added and the reaction mixture (OV-1 column, 100° C. for 2 minutes, 25° C./min to 300° C.) showed that the reaction was complete.

The reaction mixture was poured into ice/water mixture and stirred. The precipitated solid was filtered and washed with cold water, dried and dissolved in toluene. The toluene solution was washed with aqueous sodium hydroxide (10%) and water; dried and concentrated. The crude product was dissolved in toluene solution was passed through a column of alumina using toluene as eluant. Fractions containing the product were collected, combined and concentrated. The residue was recrystallized from toluene/methanol. Yield: 97.2 g (73%), white solid, M.P.: 73–75° C.)

| Components | Parts |
|---|---|
| Dispersion A - Chromogenic Material | |
| Chromogenic Material | 32.0 |
| Binder, 20% solution of Polyvinyl alcohol in water | 27.4 |
| Defoaming and dispersing agents | 0.4 |
| Water | 40.2 |
| Dispersion A1 - Chromogenic Material is ODB-2 | |
| 3-Di(n-butylamino)-6-methyl-7-anilinofluoran | |
| Dispersion A1 - Chromogenic Material is ETAC | |
| 3-(N-Ethyl-N-p-tolylamino)-6-methyl-7-anilinofluoran | |
| Dispersion B - Acidic Material | |
| Acidic Material | 42.5 |
| Binder, 20% solution of Polyvinyl alcohol in water | 21.2 |
| Defoaming and dispersing agents | 36.1 |

-continued

| Components | Parts |
|---|---|
| Dispersion B1 - Acidic Material is AP-5 | |
| 2,2-Bis(4-hydroxyphenyl)-4-methylpentane | |
| Dispersion B2 - Acidic Material is TGSA | |
| Bis(3-allyl-4-hydroxyphenyl)sulfone | |
| Dispersion C - Sensitizing Material | |
| Sensitizing Material | 42.5 |
| Binder, 20% solution of Polyvinyl alcohol in water | 21.2 |
| Defoaming and dispersing agents | 0.2 |
| Water | 36.1 |
| Dispersion C1 - Sensitizing Material | |
| Dimethyl terephthalate | |
| Dispersion C2 - Sensitizing Material is pBBP | |
| p-Benzylbiphenyl | |
| Dispersion C3 - Sensitizing Material is stearamide wax | |
| Dispersion C4 - Sensitizing Material is BZLPE-3 | |
| 2-(Benzyloxy)ethyl-[4-(benzyloxy)phenyl]ether (compound A) | |
| Coating Formulation 1 | |
| Dispersion A (Chromogenic) | 7.6 |
| Dispersion B (Acidic) | 15.0 |
| Dispersion C (Sensitizing) | 15.0 |
| Binder, 10% solution of polyvinylalcohol in water | 45.5 |
| Filler slurry, 50% in water | 19.0 |

EXAMPLE 1
Coating Formulation 1 Using
  Dispersion A1 (ODB-2)
  Dispersion B1 (AP-5)
  Dispersion C4 (BZLPE-3)

EXAMPLE 2
Coating Formulation 1 Using
  Dispersion A2 (ETAC)
  Dispersion B1 (AP-5)
  Dispersion C4 (BZLPE-3)

EXAMPLE 3
Coating Formulation 1 Using
  Dispersion A1 (ODB-2)
  Dispersion B2 (TGSA)
  Dispersion C4 (BZLPE-3)

EXAMPLE 4
Coating Formulation 1 Using
  Dispersion A2 (ETAC)
  Dispersion B2 (TGSA)
  Dispersion C4 (BZLPE-3) cl COMPARATIVE EXAMPLE 1
Coating Formulation 1 Using
  Dispersion A1 (ODB-2)
  Dispersion B1 (AP-5)
  Dispersion C1 (DMT)

COMPARATIVE EXAMPLE 2
Coating Formulation 1 Using
  Dispersion A2 (ETAC)
  Dispersion B1 (AP-5)
  Dispersion C1 (DMT)

COMPARATIVE EXAMPLE 3
Coating Formulation 1 Using
  Dispersion A1 (ODB-2)
  Dispersion B1 (AP-5)
  Dispersion C2 (PBBP)

COMPARATIVE EXAMPLE 4
Coating Formulation 1 Using
  Dispersion A2 (ETAC)
  Dispersion B1 (AP-5)
  Dispersion C2 (PBBP)

COMPARATIVE EXAMPLE 5
Coating Formulation 1 Using
  Dispersion A1 (ODB-2)
  Dispersion B1 (AP-5)
  Dispersion C3 (stearamide wax)

COMPARATIVE EXAMPLE 6
Coating Formulation 1 Using
  Dispersion A2 (ETAC)
  Dispersion B1 (AP-5)
  Dispersion C3 (stearamide wax)

COMPARATIVE EXAMPLE 7
Coating Formulation 1 Using
  Dispersion A1 (ODB-2)
  Dispersion B2 (TGSA)
  Dispersion C1 (DMT)

COMPARATIVE EXAMPLE 8
Coating Formulation 1 Using
  Dispersion A2 (ETAC)
  Dispersion B2 (TGSA)
  Dispersion C1 (DMT)

COMPARATIVE EXAMPLE 9
Coating Formulation 1 Using
  Dispersion A1 (ODB-2)
  Dispersion B2 (TGSA)
  Dispersion C2 (PBBP)

COMPARATIVE EXAMPLE 10
Coating Formulation 1 Using
  Dispersion A2 (ETAC)
  Dispersion B2 (TGSA)
  Dispersion C2 (pBBP)

COMPARATIVE EXAMPLE 11
Coating Formulation 1 Using
  Dispersion A1 (ODB-2)
  Dispersion B2 (TGSA)
  Dispersion C3 (stearamide wax)

COMPARATIVE EXAMPLE 12
Coating Formulation1 Using
  Dispersion A2 (ETAC)
  Dispersion B2 (TGSA)
  Dispersion C3 (stearamide wax)

| Coating Formulation 2 | Parts |
|---|---|
| Dispersion A (Chromogenic) | 7.6 |
| Dispersion B (Acidic) | 15.0 |
| Dispersion C (Sensitizing) | 0.0 |
| Binder, 10% solution of polyvinylalcohol in water | 45.5 |
| Filler slurry, 50% in water | 19.0 |

COMPARATIVE EXAMPLE 13
Coating Formulation 2 Using
Dispersion A1 (ODB-2)
Dispersion B1 (AP-5)

COMPARATIVE EXAMPLE 14
Coating Formulation 2 Using
Dispersion A2 (ETAC)
Dispersion B1 (AP-5)

COMPARATIVE EXAMPLE 15
Coating Formulation 2 Using
Dispersion A1 (ODB-2)
Dispersion B2 (TGSA)

COMPARATIVE EXAMPLE 16
Coating Formulation 2 Using
Dispersion A2 (ETAC)
Dispersion B2 (TGSA)

The examples were coated at 3.0 gm/m². A PVA topcoat was applied at 3.5 gm/m². The then printed on the ATLANTEK model 300. The optical density was a McBeth II densitometer. The results are in the following chart.

| Example # | McBeth Intensity at 12.0 mj/mm² | McBeth Intensity at 31.8 mj/mm² |
|---|---|---|
| 1 | 0.56 | 1.38 |
| 2 | 0.26 | 1.30 |
| 3 | 0.99 | 1.44 |
| 4 | 0.73 | 1.40 |
| Comparative 1 | 0.23 | 1.40 |
| Comparative 2 | 0.10 | 1.30 |
| Comparative 3 | 0.28 | 1.40 |
| Comparative 4 | 0.11 | 1.01 |
| Comparative 5 | 0.31 | 1.39 |
| Comparative 6 | 0.10 | 1.43 |
| Comparative 7 | 0.44 | 1.43 |
| Comparative 8 | 0.18 | 1.32 |
| Comparative 9 | 0.36 | 1.42 |
| Comparative 10 | 0.27 | 1.33 |
| Comparative 11 | 0.52 | 1.43 |
| Comparative 12 | 0.17 | 1.14 |
| Comparative 13 | 0.20 | 1.28 |
| Comparative 14 | 0.11 | 0.96 |
| Comparative 15 | 0.32 | 1.36 |
| Comparative 16 | 0.11 | 0.83 |

The principles, preferred embodiments, and modes of preparation the present invention have been described in the foregoing specification. The invention which is intended to be protected herein, however, it is not to be construed as limited to the particular forms disclosed, since these are to be regarded as illustrative rather than restrictive. Variations and changes can be made by those skilled in the art without departing from the spirit and scope of the invention.

What is claimed is:

1. A compound of the formula:

(I)

wherein P is

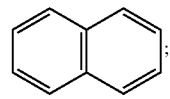

wherein $R_1$, is selected from hydrogen and aralkoxy,
wherein $R_2$ is aralkoxyalkoxy,
said alk moieties each independently being from one to eight carbons, said ar moieties each independently being unsubstituted or substituted by alkyl ($C_1$–$C_8$), alkoxy ($C_1$–$C_8$) or halogen.

2. The unsymmetrical phenyl compound

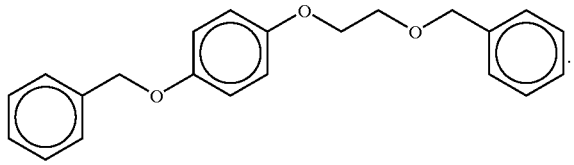

3. The unsymmetrical phenyl compound

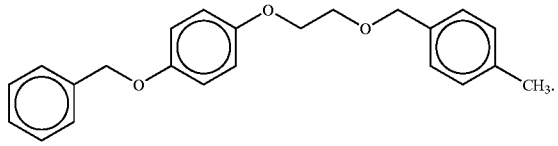

4. The unsymmetrical phenyl compound

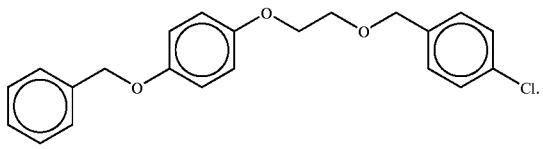

5. An unsymmetrical naphthyl compound of the formula:

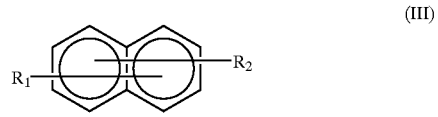

(III)

wherein $R_1$ is selected from hydrogen, alkoxy, aralkoxy,
wherein $R_2$ is aralkoxyalkoxy or alkylalkoxyalkoxy,
said alk moieties each independently being from one to eight carbons, said ar moieties each independently being unsubstituted or substituted by alkyl ($C_1$–$C_8$), alkoxy ($C_1$–$C_8$) or halogen.

6. The compound according to claim 5, wherein the unsymmetrical naphthyl compound according to formula III is

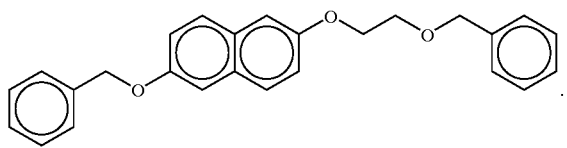

7. The compound according to claim 5, wherein the unsymmetrical naphthyl compound according to formula III is

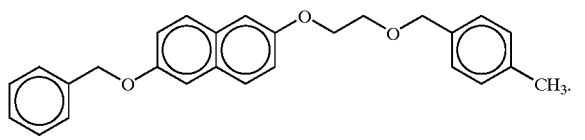

8. The compound according to claim 5, wherein the unsymmetrical naphthyl compound according to formula III is

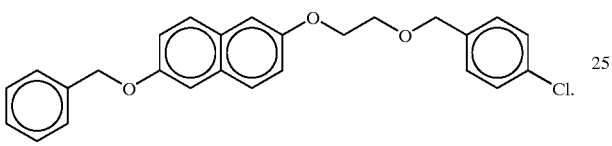

9. The compound according to claim 5, wherein the unsymmetrical naphthyl compound according to formula III is

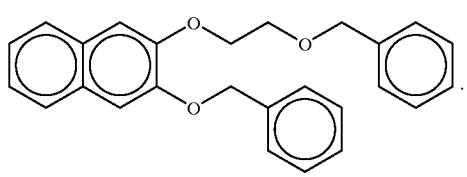

10. The compound according to claim 5, wherein the unsymmetrical naphthyl compound according to formula III is

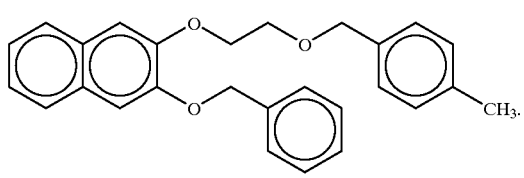

11. The compound according to claim 5, wherein the unsymmetrical naphthyl compound according to formula III is

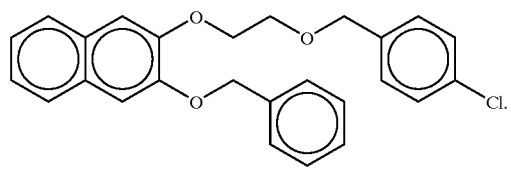

12. The compound according to claim 5, wherein the unsymmetrical naphthyl compound according to formula III is

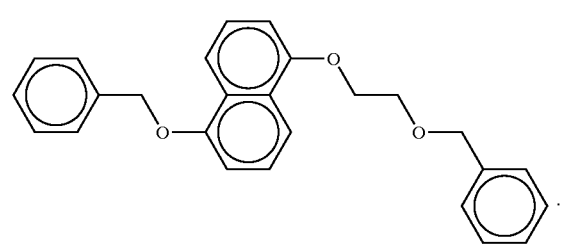

13. The compound according to claim 5, wherein the unsymmetrical naphthyl compound according to formula III is

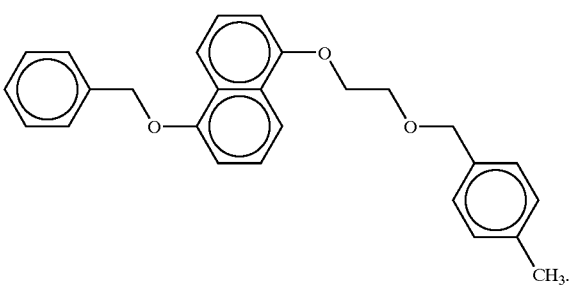

14. The compound according to claim 5, wherein the unsymmetrical naphthyl compound according to formula III is

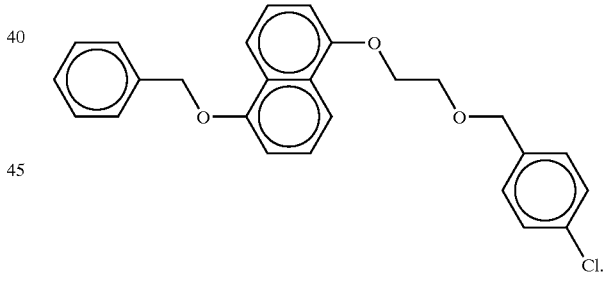

15. The compound according to claim 5, wherein the unsymmetrical naphthyl compound according to formula III is

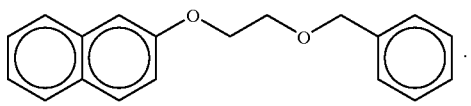

16. The compound according to claim 5, wherein the unsymmetrical naphthyl compound according to formula III is

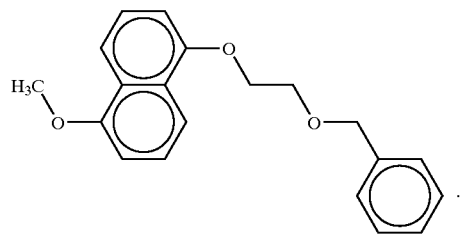
17. The compound according to claim 5, wherein the unsymmetrical naphthyl compound according to formula III is
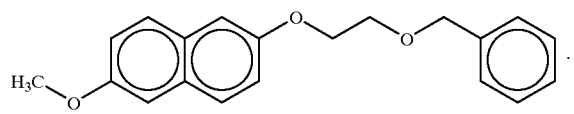
18. The compound according to claim 5, wherein the unsymmetrical naphthyl compound according to formula III is
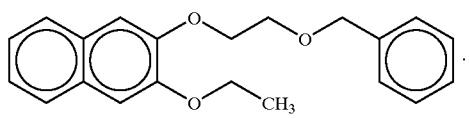
19. The compound according to claim 5, wherein the unsymmetrical naphthyl compound according to formula III is
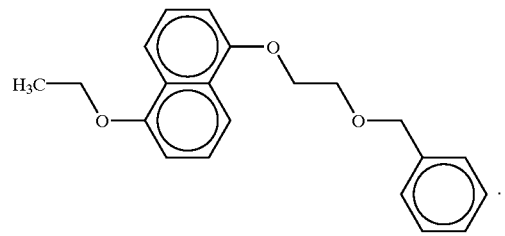
* * * * *